(12) United States Patent
Eitzinger et al.

(10) Patent No.: US 10,434,729 B2
(45) Date of Patent: *Oct. 8, 2019

(54) DEVICES AND METHODS FOR DEPOSITING REINFORCING FIBER TAPES AND DETECTING LAYING ERRORS

(71) Applicant: AIRBUS DEFENCE AND SPACE GMBH, Ottobrunn (DE)

(72) Inventors: Christian Eitzinger, Gmunden (AT); Franz Engel, Munich (DE); Tilman Orth, Munich (DE); Christian Weimer, Munich (DE)

(73) Assignee: Airbus Defence and Space GmbH, Taufkirchen (DE)

( * ) Notice: Subject to any disclaimer, the term of this patent is extended or adjusted under 35 U.S.C. 154(b) by 253 days.

This patent is subject to a terminal disclaimer.

(21) Appl. No.: 15/198,976

(22) Filed: Jun. 30, 2016

(65) Prior Publication Data
US 2017/0001384 A1    Jan. 5, 2017

(30) Foreign Application Priority Data

Jun. 30, 2015 (DE) .................. 10 2015 008 313

(51) Int. Cl.
*B29C 70/38* (2006.01)
*B29C 35/08* (2006.01)
(Continued)

(52) U.S. Cl.
CPC ........ *B29C 70/384* (2013.01); *B29C 35/0805* (2013.01); *B29C 70/38* (2013.01);
(Continued)

(58) Field of Classification Search
CPC ..... B29C 70/38; B29C 70/382; B29C 70/384; B29C 70/386; B29C 70/54;
(Continued)

(56) References Cited

U.S. PATENT DOCUMENTS 6,451,152 B1 * 9/2002 Holmes ................ B23K 26/034
156/173
8,668,793 B2   3/2014 Engelbart et al.
(Continued)

FOREIGN PATENT DOCUMENTS

DE   10 2011 051 071     12/2012
EP         2 620 269      7/2013
(Continued)

OTHER PUBLICATIONS

German Office Action with English Translation for Application No. 10 2015 008 313 dated Nov. 2, 2015.
(Continued)

*Primary Examiner* — George R Koch
(74) *Attorney, Agent, or Firm* — Jenkins, Wilson, Taylor & Hunt, P.A.

(57) ABSTRACT

Devices and methods are disclosed for depositing reinforcing fiber tapes and detecting laying errors. Automatic depositing of reinforcing fiber tapes on a support can occur by a laying head and at least one roller assigned to the laying head. At least one radiation source and/or at least one sensor is integrated into the at least one roller for the detection of laying errors, and this roller is transmissive at least by region for a radiation emitted by the radiation source.

17 Claims, 1 Drawing Sheet

(51) Int. Cl.
  B29C 70/54 (2006.01)
  G01N 21/95 (2006.01)
  *G01N 21/84* (2006.01)
  *B29K 105/08* (2006.01)
  *B29K 307/04* (2006.01)

(52) U.S. Cl.
  CPC .............. B29C 70/54 (2013.01); G01N 21/95 (2013.01); *B29K 2105/08* (2013.01); *B29K 2307/04* (2013.01); *G01N 2021/8472* (2013.01)

(58) Field of Classification Search
  CPC ............ B29C 35/0805; B29K 2105/08; B29K 2307/04; G01N 2021/8472
  See application file for complete search history.

(56) References Cited

U.S. PATENT DOCUMENTS

| | | | |
|---|---|---|---|
| 9,302,871 B2 | 4/2016 | Breineder et al. | |
| 9,772,295 B2* | 9/2017 | Engel | G01N 21/8806 |
| 2003/0145932 A1* | 8/2003 | Holmes | B23K 26/032 |
| | | | 156/64 |
| 2008/0157437 A1* | 7/2008 | Nelson | B29C 70/38 |
| | | | 264/405 |
| 2010/0300600 A1* | 12/2010 | Bichsel | B29C 70/40 |
| | | | 156/64 |
| 2012/0138223 A1* | 6/2012 | Fang et al. | B29C 35/0805 |
| | | | 156/275.5 |
| 2012/0312471 A1* | 12/2012 | Harbaugh | B32B 37/0046 |
| | | | 156/322 |
| 2014/0190629 A1* | 7/2014 | Benson | B29C 70/388 |
| | | | 156/272.2 |
| 2016/0114536 A1* | 4/2016 | Engel | G01N 21/8806 |
| | | | 156/64 |

FOREIGN PATENT DOCUMENTS

| EP | 2 918 400 | | 9/2015 |
| EP | 3 015 851 A1 | | 5/2016 |
| WO | WO 2013/104600 A1 | | 7/2013 |

OTHER PUBLICATIONS

Oromiehie et al., "In situ process monitoring for automated fibre placement using fibre Bragg grating sensors," SHM. Structural Health Monitoring, vol. 15, No. 6, The Authors 2016, DOI: 10.1177/1475921716658616, pp. 1-9, 2016.
European Search Report for Application No. 16176544.1 dated Nov. 9, 2016.

* cited by examiner

DEVICES AND METHODS FOR DEPOSITING REINFORCING FIBER TAPES AND DETECTING LAYING ERRORS

CROSS-REFERENCE TO RELATED APPLICATION

This application claims priority to DE 10 2015 008 313.9 filed Jun. 30, 2015, the entire disclosure of which is incorporated by reference herein.

TECHNICAL FIELD

The disclosure herein relates first to a device for automatically depositing reinforcing fiber tapes on a support by a laying head and at least one roller assigned to the latter.

In addition, the disclosure herein relates to a method for detection of laying errors in the automatic depositing of reinforcing fiber tapes by a device.

BACKGROUND

Contemporary manufacturing of lightweight components with high mechanical strength usually employs carbon fiber-reinforced plastics, such as CFRP. For efficient production of CFRP components with complex geometries, the so-called AFP method (automated fiber placement method), among others, is used in this context. Here the narrow tapes of carbon fibers are deposited by a laying head successively side by side and one above the other on a support and fixed in a suitable manner. At the end of the generally fully automatic laying process the reinforcing fiber structure produced in this way is preferably infiltrated with a curable plastic and cured. Alternatively, tapes of carbon fibers with a pre-impregnated curable plastic (so-called prepregs) may also be deposited fully automatically by the laying head on a support, such that the fixing of the position of the dry carbon fiber tapes and their subsequent infiltration with the curable plastic can be omitted.

For reasons of quality assurance an optical detector system arranged at the laying head is employed which performs non-contact detection of possible laying errors or verifies the compliance with specified requirements. Typical laying errors or quality characteristics, which are to be identified, are, for example, gaps between the CFRP ribbons, overlappings, contorsions, breaks, frayings, impurities, so-called fuzzballs, splicing zones, sections made too early or too late or missing CFRP ribbons.

SUMMARY

Thus, it is one idea of the disclosure herein to provide a device for automatically depositing reinforcing fiber tapes on a support, where the possible laying error is detectable with high accuracy and reliability. Moreover, it is another idea of the disclosure herein to provide a method for the improved detection of laying errors in the AFP process.

According to the disclosure herein, for the detection of laying errors at least one radiation source and/or at least one sensor is integrated into the at least one roller and this roller is at least transmissive in regions for radiation emitted by the radiation source.

Hereby, a fully automatic detection of laying errors is possible already during the laying operation, such that the optical inspection to be elsewise performed manually after the depositing of a layer of reinforcing fiber tapes can be omitted. Because of the direct integration of the measurement system consisting of or comprising the radiation source and the sensor into the roller, the movement space of the laying head is hardly restricted. In addition, due to the immediate vicinity of the measurement system to the current laying location, a significant increase of the quality in the detection of laying errors is achievable. An electronic camera sensitive to radiation emitted by the radiation or a sensor array can be used as a sensor, for example. In the event that the installation space within the roller is limited, the sensor or the radiation source can be positioned externally to the roller. In the event that the radiation source is arranged externally to the roller, the radiation can be, for example, coupled into the roller by a radiation guide. Furthermore, the reflected radiation can also be decoupled from the roller by a radiation guide and provided to a sensor arranged externally to the roller. The reinforcing fiber tapes can be both dry and pre-impregnated.

In case of a favorable technical development the radiation emitted by the at least one radiation source and reflected by the at least one deposited reinforcing fiber tape as diffuse and/or direct reflection radiation can be detected by the at least one sensor for the detection of laying errors.

As a result, a contactless and reliable detection of laying errors is possible. For the detection of laying errors the reflection properties of the light reflected by the reinforcing fiber tapes are used as physical basis quantity. The fact that in addition to the color (so-called "albedo") of the surface the angle of inclination to the radiation source and to the sensor has an influence on brightness as well, may be utilized here. By a suitable mathematical/geometrical model it is possible to deduce the form of the surface from the brightness in several illumination directions.

In a further advantageous embodiment, the at least one radiation source emits electromagnetic radiation in the visible wavelength range between 200 nm to 800 nm.

Hereby, the scanning of the surface of the deposited reinforcing fiber tapes can be performed with radiation the wavelength of which is ideally suited for the detection of laying errors. The wavelength of the radiation emitted by the radiation source is in a range between the far infrared and the far ultraviolet. Preferably, the at least one radiation source emits radiation or light, respectively, in a wavelength range visible to the human eye.

According to an advantageous development the at least one radiation source is in particular a light-emitting diode, a laser diode or a laser.

Hereby, a variety of illumination options is available. The radiation source can irradiate or illuminate, respectively, the reinforcement fiber strands with a certain frequency in a continuous or triggered manner, preferably controlled by an evaluation unit. The same applies for the control of the at least one sensor.

According to another advantageous development the roller with integrated radiation source and/or with integrated sensor is designed to be flexible at least in certain regions.

Hereby, the roller can be employed on curved supports where the altered refractive conditions are to be taken into account.

In another advantageous development, it is provided that the roller with integrated radiation source and/or with integrated sensor is designed at least in certain areas with a material that is essentially transmissive for the radiation, in particular with glass or with plastic.

As a result a largely lossless transmission of radiation emitted by the radiation source is provided. The radiation-transmissive glass or plastic can be completely transparent, opaque and/or anti-glare.

In case of an embodiment by the roller with integrated radiation source and/or with integrated sensor, the deposited reinforcing fiber tapes are compactible and/or drapable.

The roller, provided with the radiation source and the sensor, can hereby, for example, accomplish other tasks for which otherwise additional rollers would have to be provided, resulting in a cost-effective design of the device. Alternatively, in addition to the roller provided with the radiation source and the sensor, other rollers can be provided for the compaction function and/or the draping function. By a working distance which covers a sufficiently large region, the roller, simultaneously used for purposes of compaction, can also be formed in segments.

According to another embodiment the roller with integrated radiation source and/or with integrated sensor is positioned before or behind of at least another roller, especially a compacting roller or a draping roller, Hereby, a greater constructive freedom regarding the design of the roller provided with the radiation source and the sensor is provided. At the same time a leading or trailing heating of the reinforcing fiber tapes, if necessary, by the at least one radiation source and/or an additional compaction can be carried out.

According to a development the deposited reinforcing fiber tapes can be heated by the at least one radiation source.

Hereby, suitably re-impregnated reinforcing fiber tapes can be made sticky and/or cured, for example. For heating of the reinforcing fiber tapes and for detecting of laying errors two different radiation sources can be used to avoid mutual interference.

In an advantageous development measurement data produced by the at least one sensor can be evaluated by an electronic evaluation unit for the recognition of laying errors.

As a result a largely automatic evaluation and recognition of laying errors is possible. The evaluation unit can be realized, for example, with a digital computer, a PC, an FPGA, a microcontroller, a neuronal network realized by a software algorithm on a suitable hardware platform or the like. The evaluation unit detects possible laying errors based on measurement data generated by the at least one sensor by suitable algorithms and represents those online or offline in a manner suitable for a user.

The at least one sensor may preferably be a sensor of a camera for the generation of image data.

Hereby, a particularly detailed and two-dimensional detection of the reflection radiation reflected diffusely and/or directly by the surface of the reinforcing fiber tapes is possible.

In addition, the disclosure herein pertains to a method having the following steps:

a) depositing reinforcing fiber tapes by the device;

b) irradiating certain regions of at least one deposited reinforcing fiber tape by at least one radiation source;

c) detecting the reflection radiation, diffusely and/or directly reflected by the at least one deposited reinforcing fiber tape, by at least one sensor; and d) evaluating measurement data provided by the at least one sensor by an evaluation unit for the detection of laying errors.

Hereby, possible laying errors in the laying process of reinforcing tapes may automatically be determined in a simple manner with high reliability and already directly when depositing a section of a reinforcing fiber tape.

In case of an advantageous development of the method, in case of laying errors, the evaluation unit signals the occurrence of such errors and/or the depositing of reinforcing fiber tapes is interrupted.

Hereby, laying errors can be recognized early and sequence errors, that are hardly correctable with reasonable effort or not at all, i.e. the depositing of reinforcing fiber tapes on an already existing laying error already existing, can be avoided.

DETAILED DESCRIPTION

Figure 1:
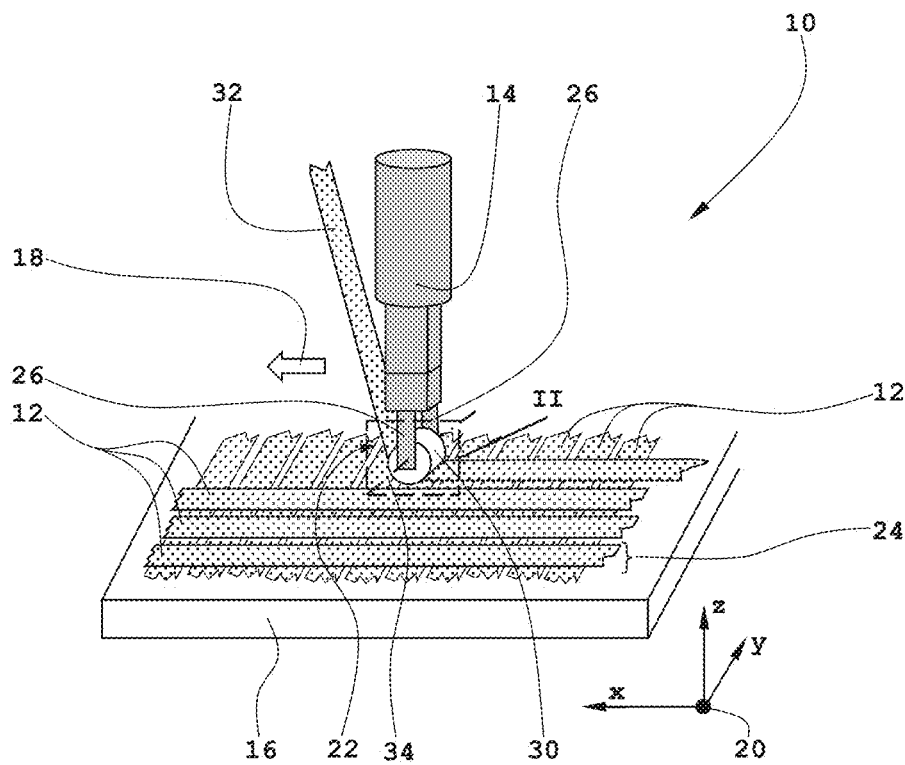
FIG. 1 shows a perspective schematic diagram of a device for automatically depositing of reinforcing fiber tapes on a support.

FIG. 1 shows a perspective schematic diagram of a device for automatically depositing reinforcing fiber tapes on a support.

A device 10 for automatically depositing of reinforcing fiber tapes 12 in the AFP process includes, among others, a laying head 14. For layered, successive depositing the reinforcing fiber tapes 12 on a support 16, the laying head 14 is freely positionable in relation to the support 16, for example by a handling device (not shown), in particular a standard industrial robot with a variety of degrees of freedom. Narrow carbon fiber tapes or CFRP ribbons, respectively, are used as reinforcing fiber tapes 12. The reinforcing fiber tapes 12 may be dry or pre-impregnated at least in sections with a suitable plastic. The support 16 may have a shape that differs from the planar form exemplarily shown here, that has, for example, any two-dimensional curved or at least partially convex or concave curved surface geometry. In this purely exemplary geometry, the laying head 14 moves in a laying direction 18 parallel to an x-axis of a coordinate system 20 spaced apart to the support 16 or to the reinforcing fiber tapes 12 already deposited thereon. Basically, the laying head 14 is automatically movable on any straight or curved paths freely in space in relation to the support 16.

At a free end 22 of the laying head 14, which is directed to a top layer 24 of already deposited reinforcing fiber tapes 12 or to the support 16, respectively, there is a cylindrical roller 30 rotatably mounted in a fork-shaped mounting 26 for guiding or deflecting, respectively, a reinforcing fiber tape 32 to be currently deposited. If necessary, the compacting or the pressing, respectively, and/or the draping of the reinforcing fiber tapes 12 already placed on the support 16 can be done by this roller 30. According to the disclosure herein a sensor not shown here and/or a radiation source is directly integrated into this roller 30 for detecting possible laying errors. An axis of rotation 34 of the roller 30 runs, for example, transversely or at right angles to the laying direction 18 or the x-axis, respectively, of the coordinate system 20.

Figure 2:
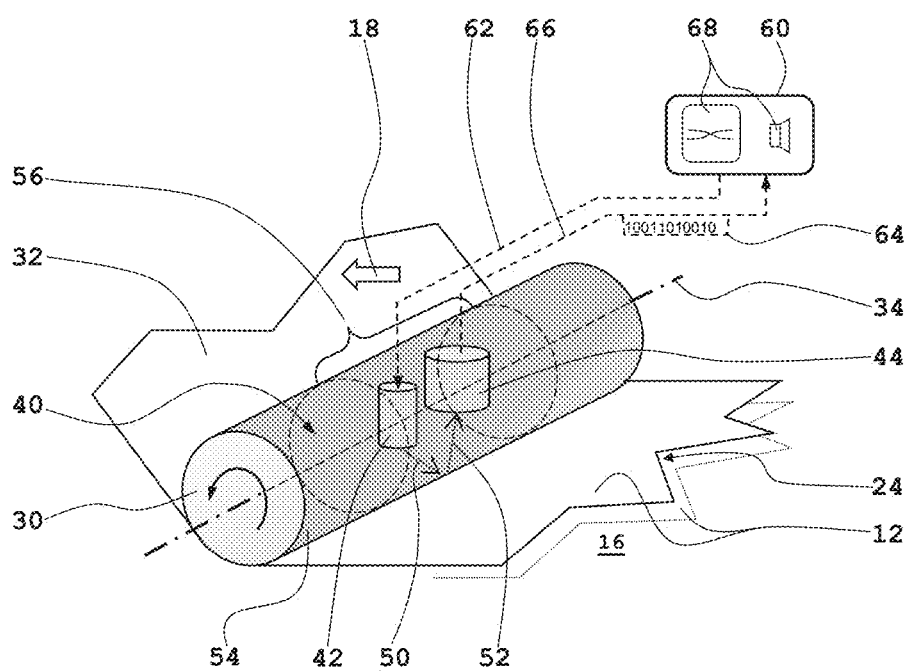
FIG. 2 shows an enlarged representation of Section II of FIG. 1.

FIG. 2 illustrates an enlarged representation of the Section II of FIG. 1.

Due to the roller 30 rotatably mounted around the axis of rotation 34—as indicated by the black rotation arrow—the reinforcing fiber tape 32 to be deposited and currently drawn off a supply reel (not shown), is at least guided or deflected, respectively, and deposited on the support 16 and forms the reinforcing fiber tape 12 thereon. By the roller 30 or with further (not shown) rollers, the reinforcing fiber tape 12 can be compacted and/or draped, if necessary. The rollers not shown in the drawings may be, for example, so-called compacting rollers or pressure rollers, respectively, or draping rollers, which can be arranged in relation to the laying direction 18 or to the moving direction, respectively, of the roller 30 in relation to the support 16—each depending on the function to be assumed as draping or compacting roller—before or behind the roller 30.

In an interior space 40, here merely exemplarily indicated as being hollow cylindrical, of the roller 30 a radiation source 42 and a sensor 44 are preferably integrated. By the radiation source 42 electromagnetic radiation 50 in a wavelength range of 1 mm (far infrared) up to 200 nm (far ultraviolet) is generated and irradiated onto the at least one reinforcing fiber tape 32 or partially onto the top layer 24 of the deposited reinforcing fiber tapes 12, respectively.

The radiation 50 emitted by the radiation source 42 is reflected by the at least one reinforcing fiber tape 12 of the top layer 24 as diffuse and/or direct reflection radiation 52 and impinges on the sensor 44 which is designed to be particularly sensitive for this very wavelength range.

In order to have the radiation 50 or the reflection radiation 52, respectively, pass the roller 30 in a substantially unimpeded manner, the roller 30 is configured to be at least partially transmissive, i.e. transmissive for the radiation 50 and the reflection radiation 52. For this purpose a cylindrical outer shell surface 54 of the roller 30 has here a peripheral transmissive region 56 which is largely transmissive for the radiation 50 or the reflection radiation 52. This cylindrical region 56 can, for example, be formed from glass or from radiation-transmissive plastics. Alternatively, the entire roller 30 can also be designed to be transmissive. Furthermore, it is conceivable to design the roller 30 to be flexible at least in sections, in order to allow a rolling thereof on a curved substrate in case of larger roller dimensions.

The radiation source 42 as well as the sensor 44 are arranged here, for example, to be rotationally fixed in relation to the axis of rotation 34, where through the region 56 extending over the entire periphery, holding the function of a continuous "window", independent of the respective rotational position of the roller 30, always a free passage of the radiation 50 or the reflection radiation 52, respectively, is given, such that a continuous detection of laying errors is possible.

Furthermore, a variety of peripheral, preferably evenly spaced window-like recesses for the passage of the radiation 50 or the reflection radiation 52, respectively, can be introduced into the outer shell surface 54 of the roller 30. However, due to the continuously rotating roller 30 and the material webs each remaining between two neighboring window-like recesses in case of a rotationally fixed arranged radiation source 42 and a rotationally fixed positioned sensor 44 brief periodic interruptions of the radiation 50 or the reflection radiation 52, respectively, may occur so that continuous detection of laying errors may not be guaranteed.

The radiation source 42 is preferably controlled by an evaluation unit 60, as indicated with a line 62, while the measurement data 64 produced by the sensor 44 is made available to the evaluation unit 60 via another line 66 for detailed evaluation and analysis. The reflection radiation 52 reflected by the at least one reinforcing fiber tape 12 allows in conjunction with the evaluation unit 60 a very reliable and detailed detection as well as a type differentiation of possibly occurring laying errors of the type described above. For this purpose a variety of suitable mathematical algorithms is stored in the evaluation unit 60.

The at least one radiation source 42 is preferably constructed with a light-emitting diode, a laser diode, with a laser or another compact illuminating means. The at least one sensor 44 can, for example, be realized with an electronic camera (CCD camera) or with a two-dimensional sensor array. In the event that the sensor 44 is formed with a camera, the measurement data 64 is preferably digital image data. The evaluation unit 60 is preferably implemented with a universal, digital computing unit, especially with a PC, a hardwired FPGA, a microcontroller, a digitally simulated neuronal network or the like.

As required, the radiation source 42 or the sensor 44 can also be arranged outside of the roller 30, which can be of advantage especially in case the dimensions of the interior space of the roller 30 are too small. In such a constellation the radiation 50 or the reflection radiation 52, respectively, can be decoupled from or coupled to the roller 30 by suitable radiation guides or waveguides.

Since controlling the radiation source 42 is performed preferably also by the evaluation unit 60, a variety of options not shown in the drawings for irradiating or illuminating the at least one deposited reinforcing fiber tape 12 or the top layer 24 of the deposited reinforcing fiber tapes 12, respectively, by the roller 30 at least partially, and for supplying the reflection radiation 52 to the sensor 44 in a suitable way.

Thus, two or more radiation sources can be connected alternatingly by the evaluation unit 60, where digital measurement data 64 or image data recorded with the different radiation sources from the sensor 44, respectively, are analyzed together and the different radiation directions are generated by suitable geometric arrangement of the radiation sources. Alternatively, the different radiation sources may be generated by diffraction or interference. Further, the at least one radiation source 42 generates a local bright/dark transition and the sensor 44 acquires measurement data 64 or this image data, respectively, specifically in the region of this transition. Furthermore, a narrow line not shown can be projected by the radiation source 42 onto the deposited reinforcing fiber tape 12, the course of which can be detected with the aid of the sensor 44 and be subject to a thorough analysis by the evaluation unit 60. In addition, two or more radiation sources can be used, the radiation of which has different frequencies or wavelengths, respectively, where the evaluation is done by extraction and analysis of the single color channels, detected by the at least one sensor, by the evaluation unit 60.

The mathematical algorithms (digital image analysis) required for the detection of laying errors on the basis of measurement data 64 provided by the contactless optical sensor 44 are sufficiently familiar to the person skilled in the art from prior art.

Furthermore, the reinforcing fiber tapes 12 may be heated by the radiation source 42 or another radiation source not shown to become adhesive and/or, in the case of reinforcing fiber tapes 12 suitably pre-impregnated with plastic, to be cured as well, whereby the production of CFRP moldings in the AFP process may be made significantly more efficient.

In the course of the method according to the disclosure herein, the reinforcing fiber tapes 12 are automatically stored by the device 10 on the support 16. At the same time the at least one reinforcing fiber tape 12 is irradiated at least in regions by the at least one radiation source 42 which may preferably be directly integrated in the roller 30. In parallel therewith the detection of the reflection radiation 52, diffusely and/or directly reflected by means from the at least one deposited reinforcing fiber tape 12, is done by the sensor 44, preferably also integrated into the roller 30, as well as the numerical evaluation of this supplied measurement data 64 by the electronic evaluation unit 60 for the detection of possible laying errors. In addition, it is also possible to determine, besides the presence of a laying error, the kind or type thereof, respectively, by the evaluation unit 60.

In the event that a laying error is detected, it is possible, for example, through an optical and/or acoustical signaling device 68 assigned to the evaluation unit 60, to make a corresponding notice to a user and/or to automatically interrupt or terminate altogether the entire laying process without requiring another external intervention.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A device for automatically depositing of reinforcing fiber tapes on a support by a laying head, the device comprising:
    at least one roller assigned to the laying head;
    at least one radiation source; and
    at least one sensor,
    wherein, for detection of laying errors, the at least one radiation source and the at least one sensor are integrated into the at least one roller,
    wherein the at least one roller is transmissive for radiation emitted by the radiation source, at least in regions thereof, and
    wherein radiation emitted from the at least one radiation source and reflected from at least one deposited reinforcing fiber tape as diffuse and/or direct reflection radiation is detectable by the at least one sensor for the detection of laying errors.

2. The device of claim 1, wherein the at least one radiation source is configured to emit electromagnetic radiation in a wavelength range between 1 mm and 200 nm.

3. The device of claim 1, wherein the at least one radiation source is a light-emitting diode, a laser diode, or a laser.

4. The device of claim 1, wherein the at least one roller is formed to be at least partially flexible.

5. The device of claim 4, wherein the at least one roller is at least partially formed with a material essentially transmissive for the radiation.

6. The device of claim 1, wherein the deposited reinforcing fiber tapes are compactible and/or drapable by the at least one roller.

7. The device of claim 1, wherein the at least one roller is positioned before or behind a compacting roller or a draping roller.

8. The device of claim 1, wherein the deposited reinforcing fiber tapes can be heated by the at least one radiation source.

9. The device of claim 1, wherein measurement data, generated by the at least one sensor, can be evaluated by an electronic evaluation unit for recognition of laying errors.

10. The device of claim 9, wherein the at least one sensor is a camera for generation of image data.

11. The device according to claim 1, wherein the at least one roller comprises an outer shell surface having a plurality of evenly spaced window-like recesses for the passage of radiation formed therein.

12. The device according to claim 1, wherein the at least one roller comprises an outer shell surface having a peripheral transmissive region which is transmissive for radiation.

13. A method for detecting laying errors in automatic deposition of reinforcing fiber tapes by a device for automatically depositing of reinforcing fiber tapes on a support by a laying head, the device comprising at least one roller assigned to the laying head, at least one radiation source, and at least one sensor, wherein the at least one radiation source and the at least one sensor are integrated into the at least one roller, the at least one roller being transmissive for radiation emitted by the radiation source, at least in regions thereof;
    the method comprising:
        depositing reinforcing fiber tapes by the at least one roller;
        irradiating at least one deposited reinforcing fiber tape, by the at least one radiation source, in regions thereof;
        detecting the reflection radiation, diffusely and/or directly reflected by the at least one deposited reinforcing fiber tape, by the at least one sensor; and
        evaluating measurement data generated by the at least one sensor by an evaluation unit for the detection of laying errors.

14. The method of claim 13, wherein, in case of laying errors, the evaluation unit signals occurrence of such errors and/or the depositing of reinforcing fiber tapes is interrupted.

15. The method of claim 13, wherein irradiating the at least one deposited reinforcing fiber tape comprises one or more of:
    projecting of a narrow line onto the deposited reinforcing fiber tape;
    alternating irradiation using two or more radiation sources; and
    irradiating, by two or more radiation sources, the radiation of which has different frequencies or wavelengths, respectively.

16. The method of claim 13, wherein the at least one roller is positioned before or behind a compacting roller or a draping roller.

17. The method of claim 13, wherein irradiating the at least one deposited reinforcing fiber tape comprises heating the reinforcing fiber tape.

* * * * *